(12) United States Patent
Andjelic et al.

(10) Patent No.: US 7,754,233 B2
(45) Date of Patent: Jul. 13, 2010

(54) METHOD OF PREVENTING POST-OPERATIVE SURGICAL ADHESION

(75) Inventors: Sasa Andjelic, New York, NY (US); Rao S. Bezwada, Whitehouse Station, NJ (US); Dennis D. Jamiolkowski, Long Valley, NJ (US)

(73) Assignee: Ethicon, Inc., Somerville, NJ (US)

( * ) Notice: Subject to any disclaimer, the term of this patent is extended or adjusted under 35 U.S.C. 154(b) by 1574 days.

(21) Appl. No.: 10/934,066

(22) Filed: Sep. 3, 2004

(65) Prior Publication Data

US 2006/0051398 A1    Mar. 9, 2006

(51) Int. Cl.
*A61F 2/02* (2006.01)
*C08G 63/02* (2006.01)
*C08G 63/08* (2006.01)
*C08G 63/82* (2006.01)

(52) U.S. Cl. .................. 424/423; 525/437; 528/272; 528/354; 528/359

(58) Field of Classification Search .................. None
See application file for complete search history.

(56) References Cited

U.S. PATENT DOCUMENTS

| | | | |
|---|---|---|---|
| 3,997,512 A | 12/1976 | Casey et al. | |
| 4,048,256 A | 9/1977 | Casey et al. | |
| 4,076,798 A | 2/1978 | Casey et al. | |
| 4,095,600 A * | 6/1978 | Casey et al. | .................. 606/230 |
| 4,118,470 A | 10/1978 | Casey et al. | |
| 4,122,129 A | 10/1978 | Casey et al. | |
| 4,938,763 A | 7/1990 | Dunn et al. | |
| 5,442,033 A | 8/1995 | Bezwada | |
| 5,464,929 A | 11/1995 | Bezwada et al. | |
| 5,599,852 A | 2/1997 | Scopelianos et al. | |
| 5,618,552 A | 4/1997 | Bezwada et al. | |
| 5,644,002 A | 7/1997 | Cooper et al. | |
| 5,653,992 A | 8/1997 | Bezwada et al. | |
| 5,688,900 A | 11/1997 | Cooper et al. | |
| 5,696,178 A | 12/1997 | Cooper et al. | |
| 5,728,752 A | 3/1998 | Scopelianos et al. | |
| 5,736,589 A | 4/1998 | Cooper et al. | |
| 5,824,333 A | 10/1998 | Scopelianos et al. | |
| 6,147,168 A | 11/2000 | Jamiolkowski et al. | |
| 6,224,894 B1 | 5/2001 | Jamiolkowski et al. | |
| 6,403,655 B1 | 6/2002 | Bezwada | |
| 6,716,251 B1 | 4/2004 | Asius et al. | |
| 2006/0051398 A1 | 3/2006 | Andjelic et al. | |
| 2008/0055086 A1 | 3/2008 | Cantatore et al. | |

* cited by examiner

*Primary Examiner*—Carlos A Azpuru
(74) *Attorney, Agent, or Firm*—David R. Crichton

(57) ABSTRACT

A method for preventing adhesion using a co-polyester comprising the reaction product of a polycondensation polyester and at least one lactone, wherein the polycondensation polyester comprises the reaction product of diglycolic acid and/or a derivative thereof and ethylene glycol; and the co-polyester comprises about 40 to 50% by weight of the polycondensation polyester based on the total weight of the co-polyester.

6 Claims, No Drawings

METHOD OF PREVENTING POST-OPERATIVE SURGICAL ADHESION

FIELD OF THE INVENTION

The present invention relates to a method of preventing adhesions using an absorbable co-polyester of a polycondensation polyester and at least one lactone.

BACKGROUND OF THE INVENTION

Adhesion formation after peritoneal surgery is a major cause of postoperative bowel obstruction, in fertility, and chronic pelvic pain. In addition, adhesion formation can occur after abdominal, gynecological, cardiac, thoracic, spinal, ENT, or orthopedic (e.g. tendon, joint, and knee) surgery. Therefore, a methodology by which adhesion formulation after surgery could be reduced or prevented would be of great benefit in reducing postoperative morbidity.

The most straightforward approach to reducing the incidence of adhesion formation remains physically maintaining the adhesiogenic surfaces apart with a mechanical barrier. For example, U.S. Pat. No. 6,403,655, assigned to Ethicon, Inc., describes a method of preventing adhesion formation between tissues by placing a polyoxaester adhesion prevention barrier between such tissues. Exemplified in the disclosure are a polyoxaester of 3,6-dioxaoctanedioic acid and ethylene glycol, as well as a copolymer of polyoxaester/caprolactone/glycolide.

U.S. Pat. No. 5,644,002, also assigned to Ethicon, Inc., describes absorbable polymers and blends of polycondensation polyester and aliphatic polyesters based on lactone monomers, where the polycondensation polyester is the reaction product of diglycolic acid and an alcohol selected from selected from the group consisting of glycerol, pentaerythitol, trimethylolpropane, hydroxyl terminated poly(ethylene glycol)s, ethylene glycol, 1,2-propanediol, 1,3-propanediol, 1,4-butylene glycol, dipropylene glycol, 1,5-pentanediol, 1,6-hexanediol, 1,7-heptanediol, and 1,8-octanediol. This reference teaches that the incorporation of hydroxyl terminated poly(ethylene glycol)s in the polycondensation polyester is desirable because it leads to polymers which are useful as adhesion prevention barriers. Additionally, this reference discloses that ultrathin coatings of about 1 to about 1000 microns can be applied to tissue surfaces for the prevention of adhesions.

U.S. Pat. Nos. 3,997,512, 4,048,256, 4,076,798, 4,095,600, 4,118,470, and 4,122,129, assigned to American Cyanamid Company, describe biocompatible and absorbable polycondensation polyesters, which are the polycondensation product of diglycolic acid and glycols such as ethylene glycol, diethylene glycol, 1,2-propylene glycol, 1,3-propylene glycol, and the like. Specifically, U.S. Pat. No. 4,095,600 describes a reaction product of (a) about 2 to 50% by weight of the polycondensation polyester and (b) polyglycolic acid, based on the total weight of the polycondensation polyester and polyglycolic acid, to form a self-supporting polymeric film for use, for example, in drug delivery. This reference is silent with respect to use of the composition for adhesion prevention.

SUMMARY OF THE INVENTION

Described herein is a method for preventing adhesion using a co-polyester comprising the reaction product of a polycondensation polyester and at least one lactone, wherein the polycondensation polyester comprises the reaction product of diglycolic acid and/or a derivative thereof and ethylene glycol; and the co-polyester comprises about 40 to 50% by weight of the polycondensation polyester based on the total weight of the co-polyester.

DETAILED DESCRIPTION

The co-polyester described herein has been found to have good adhesion prevention properties. In one embodiment, the co-polyester comprises the reaction product of a polycondensation polymer and at least one lactone, wherein the polycondensation polyester comprises the reaction product of diglycolic acid and/or a derivative thereof and ethylene glycol.

In another embodiment, the polycondensation polyester comprises the reaction product of diglycolic acid and/or a derivative thereof, up to about 25 mole percent of an aliphatic diacid based on the total moles of acid, and ethylene glycol. Specifically, the aliphatic diacid may be an aliphatic alpha-omega dicarboxylic acid, including but not limited to 3,6-dioxaoctanedioic acid, 3,6,9-trioxaundecanedioic acid, and combinations thereof.

The polycondensation polyester may be synthesized by conventional techniques using conventional processes. For example, in a condensation polymerization, diglycolic acid and ethylene glycol may be polymerized in the presence of a catalyst at elevated temperatures and reduced pressures. A variety of catalysts may be used, but organometallic compounds have been found to be useful. The catalyst for the polycondensation step of the synthesis is preferably tin based, e.g., stannous octoate. The most desirable catalyst is dibutyltin oxide and is present in the diglycolic acid/ethylene glycol monomer mixture at a sufficiently effective molar ratio of monomer to catalyst, e.g., ranging from about 5,000/1 to about 100,000/1. For example, the ratio of 10,000/1 has been found to be quite suitable. The reaction is typically carried out at a temperature range from about 100° C. to about 220° C., preferably from about 140° C. to about 180° C., under an inert atmosphere until esterification of diglycolic acid is complete. Preferably, 165° C. has been found to be a desirable reaction temperature when employing a vertically stirred reactor. It should be noted that the optimum reaction temperature may be reactor and catalyst level dependent but can be found by one having only ordinary skill through the use of experiments. The first stage of the polycondensation reaction (inert gas at atmospheric pressure) is followed by polymerization under reduced pressure until the desired molecular weight and viscosity are achieved.

The weight average molecular weight of the polycondensation polymer can range from about 5,000 to about 30,000 g/mol, preferably from about 7,000 to about 20,000 g/mol, most preferably about 10,000 g/mol. This corresponds to an inherent viscosity range from about 0.25 to about 0.60 dL/g.

When the molecular weight of the polycondensation polymer is lower than about 5,000 g/mol, the molecular weight of the final co-polyester is too low to achieve the desired mechanical properties necessary for many medical device applications. Although molecular weight can be increased with increasing reaction time, it becomes increasingly difficult to achieve very high molecular weight. We have found, in general, that a molecular weight of the polycondensation polymer greater than about 30,000 g/mol, is not necessary to achieve desirable properties. One could however envision that this value is not an absolute bar. One might for instance, increase the molecular weight of the polycondensation polymer, and lower the amount of the lactone component used in the preparation of the final co-polyester.

The amount of polycondensation polyester used to prepare the co-polyester is about 40 to 50% by weight based on the total weight of the co-polyester.

Suitable lactone monomers include, but are not limited to, glycolide, lactide (l, d, dl, meso), p-dioxanone, trimethylene carbonate, epsilon-caprolactone, delta-valerolactone, beta-butyrolactone, epsilon-decalactone, 2,5-diketomorpholine, pivalolactone, alpha,alpha-diethylpropiolactone, ethylene carbonate, ethylene oxalate, 3-methyl-1,4-dioxane-2,5-dione, 3,3-diethyl-1,4-dioxan-2,5-dione, gamma-butyrolactone, 1,4-dioxepan-2-one, 1,5-dioxepan-2-one, 1,4-dioxan-2-one, 6,8-dioxabicycloctane-7-one, and combinations of two or more thereof. The preferred lactone monomer includes glycolide.

In one embodiment, the co-polyester may comprise the reaction product of a polycondensation polyester and a lactone such as glycolide.

In another embodiment, the co-polyester may comprise the reaction product of a polycondensation polyester and two or more lactones. For example, the co-polyester may comprise the reaction product of the polycondensation polyester, at least 75 mole percent glycolide based on the total moles of lactone, and a second lactone monomer.

The co-polyesters of the present invention may be conveniently synthesized by reaction of a dihydroxy poly(alkylene diglycolate) homopolymer or copolymer with a lactone by conventional techniques using conventional processes. For example, the polycondensation polyester is used as an α,ω-dihydroxy macroinitiator in a subsequent ring opening polymerization (ROP) with a lactone or a lactone mixture. The lactone monomers are copolymerized into the polycondensation polyester in the presence of a conventional organometallic catalyst at elevated temperatures. The catalyst for the ROP may be already present as residual catalyst in the polycondensation polyester or may be additional catalyst added in this second step of the synthesis. A suitable catalyst added at the time of the ROP can be an organometallic catalyst. The ring-opening organometallic catalyst is preferably tin based, e.g., stannous octoate, and is present in a sufficiently effective amount in the monomer mixture, preferably at a molar ratio of lactone monomer-to-catalyst ranging from about 20,000/1 to infinity (i.e. no additional catalyst used). Thus one might utilize a tin-IV compound such as dibutyltin oxide at a diacid, for instance, diglycolic acid-to-catalyst ratio of about 10,000/1 to prepare the polycondensation polyester and then add a tin-II compound such as stannous octoate at a lactone-to-added-catalyst molar ratio of about 240,000/1 at the time of the ring opening polymerization. The co-polyesters of the present invention may be synthesized alternately with no additional catalyst being added at the time of the ROP as described in Example 3A.

The ROP step can be immediately conducted in the same reactor as that used to synthesize the polycondensation polyester immediately after the completion of the polycondensation step, if the reactor can provide adequate heat transfer and agitation. The lactone or lactone mixture can be added as a solid, a slurry, or in molten form. Alternately, the ROP can be conducted in a separate reactor at a later date, or in the reactor used for the polycondensation polyester at a later date. If this is the case, the polycondensation polyester is discharged from its reactor and is stored in an environment that minimizes water pick up and hydrolysis. In the case of adding glycolide monomer, the monomer can be added as a solid. The reactor is closed and the pressure reduced. The reactor is usually held under vacuum for a prolonged period of time, for instance overnight, to allow drying. Nitrogen is then introduced into the reactor to bring the pressure to slightly greater than one atmosphere, and the purge cycle repeated for a total of three times. The temperature of the reaction mass is brought up to 130° C. Once at this temperature, the agitator is activated. The temperature is then increased to 150° C. to complete the mixing. This mixing step is essential to produce the co-polyesters of the present invention as inadequate mixing tends to allow the formation of homopolymeric sequences which can then crystallize to an extent greater than optimum. To ensure that reactants are fully mixed, in-situ spectroscopic probes (such as Near-Infrared) can be conveniently used. If additional catalyst is to be added, it is typically added once the batch has been completely mixed. The temperature is quickly brought up to the final reaction temperature, with 210° C. being a most preferred temperature, and held there for typically 2 hours. The exact reaction conditions will depend on the catalyst and its level; final reaction temperatures can vary from about 195° C. to 235° C., and more preferably from about 200° C. to about 220° C. Reaction times can vary from about 30 minutes to a few hours, depending on the catalyst and it level, and is typically conducted until the desired conversion of monomer to polymer is achieved.

An alternate reaction scheme that has been employed to prepare the co-polyesters of the invention has involved adding the lactone as a molten stream into the reactor. Thus the polycondensation polyester is added first, typically as a molten stream and the reactor evacuated. The reactor is heated to 130° C. Molten glycolide (or other glycolide rich mixture) at a temperature of 100° C. is added to the reactor. Although the batch temperature drops slightly, it is quickly brought back up to 130° C. at which point mixing is started. At this point, the process that was described above is followed.

Under the above described conditions, the co-polyesters of polycondensation polyester and lactones, will typically have a weight average molecular weight of about 10,000 g/mol (a.k.a. Daltons) to about 100,000 g/mol, preferably about 15,000 g/mol to about 50,000 g/mol, and more preferably about 20,000 g/mol to about 40,000 g/mol, most preferably about 30,000 g/mol. These molecular weights are sufficient to provide an effective inherent viscosity, typically between about 0.30 to about 2.0 deciliters per gram (dL/g), preferably about 0.40 to about 1.0 dL/g, more preferably about 0.50 to about 0.8 dL/g and most preferably about 0.65 dL/g, as measured in a 0.1 g/dL solution of hexafluoroisopropanol (HFIP) at 25° C.

The co-polyester may be applied directly to a surgical wound site or trauma site. For example ultra-thin films of about 1 to about 1000 microns can be applied to tissue surfaces, including the lumen of tissue such as a blood vessel, or particularly over tissue that has been sutured or repaired with a mesh. Once applied, the films are useful in the treatment or prevention of adhesions. Alternatively, articles such as medical devices may be molded from the co-polyester described herein by various conventional injection and extrusion molding processes. For example, the co-polyester may be molded to form films which, when sterilized by gamma or e-beam sterilization (i.e. between 15 to 40 kGy), suffer no detrimental effect to the physical properties and are useful as adhesion prevention barriers. Alternatively, the co-polyester may be a component of a medical device, i.e., the co-polyester may form one layer of a multi-laminate hernia repair mesh, or may be suspended in a polymer solution and coated onto at least a portion of a medical device.

EXAMPLES

Example 1A and 1B provides a detailed description of the synthesis of a α,ω-dihydroxy poly(ethylene diglycolate)

homopolymer with different molecular weights. Examples 2A, 2C and 3A provide a detailed description of the reaction of α,ω-dihydroxy poly(ethylene diglycolate) homopolymer from Example 1A, with a lactone monomer, glycolide, to produce a co-polyester of the present invention. Example 2A details the preparation of a co-polyester of the present invention, an amorphous 40/60 (weight basis) poly(ethylene diglycolate-co-glycolate) co-polyester. The combined sources of tin in Example 2A result in a lactone-to-total-tin-catalyst ratio of about 19,250/1; the total tin in the final co-polyester is about 32 ppm on a weight basis. Example 2B provide a detailed description of the reaction of α,ω-dihydroxy poly(ethylene diglycolate) homopolymer from Example 1B, with a lactone monomer, glycolide, to produce a co-polyester of the present invention.

Example 1A

Synthesis of Hydroxy Terminated Poly(ethylene diglycolate) Polycondensation Polyester A twin-agitated reactor with intermeshing HELICONE patterned blades (Atlantic 10CV reactor) was employed. After charging the reactor with 10.0 kg of diglycolic acid, 13.9 kg of ethylene glycol (EG) and 1.86 grams of dibutyltin oxide catalyst, the pressure was reduced to below 1 Torr and the vacuum preserved over night. The next day vacuum was released by introducing dry nitrogen (argon can be substituted) and heating of the mixture was started. When the reactor temperature reached 150° C., the agitator speed was set to 30 RPM. Soon, a first distillate containing mostly water, an esterification by-product, appeared. The reaction was continued at 165° C. for about 2 hours until approximately all water was distilled and/or first traces of EG appeared in the distillate. After the first nitrogen/argon stage was completed, pressure was lowered gradually to full vacuum while the temperature of the batch was maintained at 165° C. A vacuum of about 30-50 mTorr was maintained throughout the rest of the reaction. Melt and solution viscosities were regularly checked to ensure a polycondensation polyester of a desired molecular weight. A hydroxy end-capped polycondensation polyester was discharged after 75 hours of reaction time under vacuum. It was a fully amorphous, colorless viscous liquid with a glass transition temperature of 3° C. Weight average molecular weight was 12,000 g/mol; the polycondensation polyester exhibited an inherent viscosity (IV) of 0.35 dL/g, as determined in HFIP at 25° C. at a concentration of 0.1 g/dL.

Example 1B

Synthesis of Hydroxy Terminated Poly(ethylene diglycolate) Polycondensation Polyester A twin-agitated reactor with intermeshing HELICONE patterned blades (Atlantic 10CV reactor) was employed. After charging the reactor with 10.0 kg of diglycolic acid, 13.9 kg of ethylene glycol (EG) and 1.86 grams of dibutyltin oxide catalyst, the pressure was reduced to below 1 Torr and the vacuum preserved over night. The next day vacuum was released by introducing dry nitrogen (argon can be substituted) and heating of the mixture was started. When the reactor temperature reached 150° C., the agitator speed was set to 30 RPM. Soon first distillate appeared containing mostly water, an esterification by-product. The reaction was continued at 165° C. for about 2 hours until approximately all water was distilled and/or first traces of EG appeared in the distillate. After the first nitrogen/argon stage was completed, pressure was lowered gradually to full vacuum while the temperature of the batch was maintained at 165° C. A vacuum of about 30-50 mTorr was maintained throughout the rest of the reaction. Melt and solution viscosities were regularly checked to ensure a polycondensation polyester of a desired molecular weight. A hydroxy end-capped polycondensation polyester was discharged after 100 hours of reaction time under vacuum. It was a fully amorphous, colorless viscous liquid with a glass transition temperature of about 8° C. Weight average molecular weight was about 20,000 g/mol; the resin exhibited an inherent viscosity (IV) of 0.55 dL/g, as determined in HFIP at 25° C. at a concentration of 0.1 g/dL.

Example 2A

The Copolymerization of an α,ω-Dihydroxy Poly(ethylene diglycolate) Homopolymer with a Lactone Monomer, Glycolide A portion of the polycondensation polyester (2.5 kg) produced in Example 1A was added into an Atlantic 8CV reactor, which is equipped with a melt tank reservoir allowing molten glycolide monomer (3.8 kg) to be added later in a liquid state. After the polycondensation polyester was charged, a vacuum of less than 1 Torr was kept over night. The next day the resin was heated to about 130° C., at which point the molten glycolide monomer was transferred from the melt tank with agitation. Agitator mixing was continued (20 RPM) and the batch temperature raised to 150° C. until full mixing was achieved. In situ, a real-time Fourier Transform Near-Infrared probe was used to confirm complete mixing of components before the addition of catalyst, stannous octoate (0.412 ml of toluene solution, glycolide to catalyst level 240,000:1). The temperature was then increased to 210° C. and the reaction was continued for another two hours. The discharged co-polyester was fully amorphous, with a colorless to slightly yellow tint, and had a glass transition temperature of 23° C. Weight average molecular weight was 27,000 g/mol and an inherent viscosity of 0.64 dL/g, as determined in HFIP at 25° C. at a concentration of 0.1 g/dL, was recorded. The composition was confirmed by NMR to be 40/60 by weight poly(ethylene diglycolate-co-glycolide).

The co-polyester was made into 5 mil thick films via compression molding and then subject to gamma sterilization at 15, 30 and 38 kGy or e-beam sterilization at 25 kGy). No detrimental effect to the physical properties was observed.

Example 2B

The Copolymerization of an αω,w-Dihydroxy Poly(ethylene diglycolate) Homopolymer with a Lactone Monomer, Glycolide A portion of the polycondensation polyester (2.5 kg) produced in Example 1B was added into an Atlantic 8CV reactor, which is equipped with a melt tank reservoir allowing molten glycolide monomer (2.5 kg) to be added later in a liquid state. After the polycondensation polyester was charged, a vacuum of less than 1 Torr was kept over night. The next day the resin was heated to about 130° C., at which point the molten glycolide monomer was transferred from the melt tank with agitation. Agitator mixing was continued (20 RPM) and the batch temperature raised to 150° C. until full mixing was achieved. In situ, a real-time Fourier Transform Near-Infrared probe was used to confirm complete mixing of components before the addition of catalyst, stannous octoate (0.412 ml of toluene solution, glycolide to catalyst level 240,000:1). The temperature was then increased to 210° C. and the reaction was continued for another two hours. The discharged co-polyester was fully amorphous, with a colorless to slightly yellow tint, and had a glass transition temperature of 22° C. Weight average molecular weight was 36,000 g/mol and an inherent viscosity of 0.81 dL/g, as determined in HFIP at 25° C. at a concentration of 0.1 g/dL, was recorded. The composition was confirmed by NMR to be 50/50 by weight poly (ethylene diglycolate-co-glycolide).

Example 2C

The Copolymerization of an α,ω-Dihydroxy Poly(ethylene diglycolate) Homopolymer with a Lactone Monomer, Glycolide A portion of the polycondensation polyester (2.5 kg) produced in Example 1A was added into an Atlantic 8CV reactor, which is equipped with a melt tank reservoir allowing molten glycolide monomer (2.5 kg) to be added later in a liquid state. After the polycondensation polyester was charged, a vacuum of less than 1 Torr was kept over night. The next day the resin was heated to about 130° C., at which point the molten glycolide monomer was transferred from the melt tank with agitation. Agitator mixing was continued (20 RPM) and the batch temperature raised to 150° C. until full mixing was achieved. In situ, a real-time Fourier Transform Near-Infrared probe was used to confirm complete mixing of components before the addition of catalyst, stannous octoate (0.412 ml of toluene solution, glycolide to catalyst level 240,000:1). The temperature was then increased to 210° C. and the reaction was continued for another two hours. The discharged co-polyester was fully amorphous, with a colorless to slightly yellow tint, and had a glass transition temperature of 19° C. Weight average molecular weight was 22,000 g/mol and an inherent viscosity of 0.53 dL/g, as determined in HFIP at 25° C. at a concentration of 0.1 g/dL, was recorded. The composition was confirmed by NMR to be 50/50 by weight poly (ethylene diglycolate-co-glycolide).

Example 3A

The Copolymerization of an α,ω-Dihydroxy Poly(ethylene diglycolate) Homopolymer with a Lactone Monomer, Glycolide The following example is similar to the Example 2A with a noted exception that additional catalyst was not added for the ring-opening portion of the synthesis and the reaction was conducted for a longer period of time. A portion of the polycondensation polyester (2.5 kg) produced in Example 1A was added into an Atlantic 8CV reactor, which is equipped with a melt tank reservoir allowing molten glycolide monomer (3.8 kg) to be added later in a liquid state. After the polycondensation polyester was charged, a vacuum of less than 1 Torr was kept over night. The next day the resin was heated to about 130° C., at which point the molten glycolide monomer was transferred from the melt tank with agitation. Agitator mixing was continued (20 RPM) and the batch temperature raised to 150° C. until full mixing was achieved. In situ, a real-time Fourier Transform Near-Infrared probe was used to confirm complete mixing of components; no additional catalyst, (e.g. stannous octoate) was added for conducting this second step, ring opening polymerization. As exemplified herein, the lactone-to-added-catalyst molar ratio was then ∞/1, the lactone-to-total-tin-catalyst ratio was about 20,900/1; the total tin in the final co-polyester was about 29.5 ppm on a weight basis. The temperature was then increased to 210° C. and the reaction was continued for another three hours. The discharged co-polyester was fully amorphous, with a colorless to slightly yellow tint, and had a glass transition temperature of 23° C. Weight average molecular weight was 25,000 g/mol and an inherent viscosity of 0.65 dL/g, as determined in HFIP at 25° C. at a concentration of 0.1 g/dL, was recorded. Composition was confirmed by NMR to be 40/60 by weight poly(ethylene diglycolate-co-glycolide).

Example 4

Two-Week Study Using an In Vivo Rabbit Hernia Sidewall Model

Animal Preparation:

The rabbits (Female, New Zealand White Rabbits, weights of approximately 3.5-5.5 kg) were fasted overnight prior to implantation. Elizabethan Collars were placed on the animals for approximately seven days post-surgery. An electric animal clipper equipped with a size 40 blade was used to depilate the surgical site. The area was vacuumed to remove clippings. The anesthetized animal was delivered to the operating table and placed in dorsal recumbency. The surgical site was prepared by wiping with alcohol followed by a surgical scrub solution (2% chlorhexidine acetate). A sterile surgical drape was then being applied to the prepared area using aseptic technique. Body weights was measured preoperatively and just prior to the end of the study.

Anesthesia:

On the day of surgery, each rabbit was pre medicated with glycopyrrolate (0.02 mg/kg, SC), approximately 15 minutes prior to anesthesia. Anesthesia was induced by using inhalation anesthesia (isoflurane at 5.0%) via facemask. Subsequent anesthesia was maintained with isoflurane (0.5-3.5% in 100% oxygen). Depth of anesthesia was monitored by heart rate and respiration as well as palpebral and paw pinch reflex, with anesthesia adjusted as needed. Intravenous access was established and Lactated Ringer's solution was administered at a rate of 11 ml/kg/hr throughout the surgical procedure.

Surgical Procedure:

A 12 cm (approximately) midline ventral abdominal incision was made approximately 4 cm caudal to the xiphoid cartilage. The cecum was exteriorized then abraded by wiping the surface ten times with a dry gauze sponge and turned 90 degrees and wiped again ten times. This procedure was continued until all aspects of the cecum had been abraded. A defect on each abdominal sidewall, approximately size 2×4.5 cm, was made lateral to and parallel with incision by sharp dissection. The defect was made approximately 2 cm lateral to the midline incision, and 3 cm caudal to the xiphoid process. A rectangular piece of control mesh fabricated from polypropylene fibers, and a composite fabricated from polypropylene mesh with a 5 mil film made from an amorphous 40/60 (weight basis) poly (ethylene diglycolate-co-glycolate) copolymer affixed to it, were sutured over each defect using a polypropylene suture (4-0) in a continuous pattern and oriented adjacent to the cecum. The abdominal wall was closed with a simple continuous suture pattern over-sewn by several simple interrupted stitches using size 3-0 synthetic absorbable suture. Subcutaneous tissues were closed with a simple continuous suture pattern using size 3-0 synthetic absorbable suture. The skin was closed with stainless steel skin staples.

Euthanasia:

Animals were euthanized at 14 days postoperatively with an intravenous injection of Euthasol (or equivalent) at a dosage of 0.3 ml/kg of body weight. The medial ear vein was used for the injection site. Following administration of the drug, a stethoscope was used to confirm that there was no detectable cardiac and respiratory function. After death had been confirmed using a stethoscope, the femoral artery was transected as a redundant confirmation of death.

Necropsy:

Necropsy evaluation was performed, and macroscopic observations of all implant sites were recorded using the scoring scheme presented below. At the time of the macroscopic evaluation, the animals were identified such that the prosecutor scoring the adhesions was blinded to treatment. Macroscopic observations of implant sites were recorded according to the scheme presented below. The left and right sites were assessed separately. The presence and location of any extraneous adhesions were recorded.

Adhesion Extent Score:
 Estimation of extent of adhesions to mesh surface:
 0=no adhesions
 1=1-25%
 2=26-50%
 3=51-75%
 4=76-100%

Adhesion Severity Score:
 Severity of most significant adhesions:
 0=no adhesions
 1=adhesion separated with minimal effort
 2=adhesion separated with moderate effort
 3=adhesion separated with difficulty Adhesion Total Score:
 Total Score=Severity Score+Extent Score Incidence:
 Percentage of sites with adhesions

TABLE 4

14 Days Study Using an In Vivo Rabbit Abdominal Sidewall Model

|  | Polypropylene Mesh (PPM) Control | Composite of PPM/5 mil Co-polyester Film of Ex. 2A |
|---|---|---|
| Adhesion Extent Score | 1.6 | 0.5 |
| Adhesion Severity Score | 1.4 | 0.6 |
| Adhesion Total Score | 3.0 (out of 7) | 1.1 (out of 7) |
| Incidence | 75% | 38% |

In this study, the adhesion characteristics of a polypropylene-based mesh are compared to those of a composite of the same mesh top-coated with a film of the co-polyester of Example 2A, which is based on diglycolic acid with a crystallinity level of zero, i.e. fully amorphous. It is clear that in comparing the control (PPM) with the composition of the present invention that the adhesion performance of the latter is far superior. It should also be noted that the only adhesion found were at the perimeter of the device and can be attributed to the polypropylene sutures used to fix the device to the abdominal wall.

Example 5

Applying the same methodology described in Example 4, but extending the Euthanasia time from 14 days to 3 month (i.e. animals were euthanized at 3 months postoperatively with an intravenous injection of Euthasol (or is equivalent) at a dosage of 0.3 ml/kg of body weight). Adhesion prevention results are reported in Tables 5A and 5B.

TABLE 5A

3 Month Studies Using an In Vivo Rabbit Abdominal Sidewall Model

| Materials | Left Abdominal Defect | | | Right Abdominal Defect | | |
|---|---|---|---|---|---|---|
|  | Extent | Severity | Total | Extent | Severity | Total |
| Polypropylene Mesh (PPM) Control | 2 | 2 | 4 | 3 | 3 | 6 |
| Composite of PPM/5 mil Co-polyester Film of Ex. 2A | 0 | 0 | 0 | 0 | 0 | 0 |
| Composite of PPM/5 mil Co-polyester Film of Ex. 2C | 0 | 0 | 0 | 2 | 2 | 4 |
| Composite of PPM/5 mil Co-polyester Film of Ex. 2B | 1 | 1 | 2 | 0 | 0 | 0 |

Note:
Extent Score is out of 4, Severity Score is out of 3 and Total Score is out of 7.

TABLE 5B

Necropsy data of in-vivo abdominal wall rabbit study including several Co-polyester Formulations on Multiple Animals/Sites (5 Animals/10 sites/Article)

| Article | Composition | Incidence (%) | Severity | Comments |
|---|---|---|---|---|
| Control | Polypropylene Mesh (PPM) Control | 80* | very strong adhesions, in 3 animals including multiple organs | due to strong adhesions the defect's surface shrunk |

TABLE 5B-continued

Necropsy data of in-vivo abdominal wall rabbit study including several Co-polyester Formulations on Multiple Animals/Sites (5 Animals/10 sites/Article)

| Article | Composition | Incidence (%) | Severity | Comments |
|---------|-------------|---------------|----------|----------|
| A | Composite of PPM/5 mil Co-polyester Film of Ex. 2A sutured with polypropylene sutures | 40 | very weak adhesions (the lowest score overall), only one edge stronger with omentum | Only edge adhesions to omentum caused by suturing |
| B | Composite of PPM/5 mil Co-polyester Film of Ex. 2C sutured with polypropylene sutures | 60 | Edge adhesions of low intensity, 2 severe including multiple organs | some inflammation, free particles in the cavity, swelling |
| C | Composite of. PPM/5 mil Co-polyester Film of Ex. 2B sutured with polypropylene sutures | 40 | all edge adhesions including one with cecum | 2 week study: no free particles in the cavity, large swelling |

Note:
*In two control animals, adhesions were extremely severe at one defect site including multiple organs, so that the other defect site was shielded and free of adhesions.

In this study, the adhesion characteristics of a polypropylene-based mesh, (PPM) are compared to those of a composite of the same mesh laminated with a 5 mil film of the co-polyesters of Examples 2A, 2B and 2C. It is clear in comparing the PPM control with the composition of the present invention, that the adhesion performance of the latter is far superior. It should also be noted that the only adhesion found were at the parameter of the device and can be attributed to the polypropylene sutures used to fix the device to the abdominal wall.

Although this invention has been shown and described with respect to detailed embodiments thereof, it will understood by those skilled in the art that various changes in form and detail thereof may be made without departing from the spirit and scope of the claimed invention.

What is claimed is:

1. A method of preventing adhesion formation between tissues comprising the step of placing between said tissues a medical device having as one of its component a fully amorphous co-polyester comprising the reaction product of a polycondensation polyester and at least one lactone,
wherein the polycondensation polyester comprises the reaction product of diglycolic acid and/or a derivative thereof and ethylene glycol; and
the co-polyester comprises about 40 to 50% by weight of the polycondensation polyester based on the total weight of the co-polyester.

2. The method according to claim 1, wherein the at least one lactone is glycolide.

3. The method according to claim 1, wherein the co-polyester comprises the reaction product of a polycondensation polyester, at least 75 mole percent glycolide based on the total moles of lactone, and a lactone selected from the group consisting of lactide (l, d, dl, meso), p-dioxanone, trimethylene carbonate, epsilon-caprolactone, delta-valerolactone, beta-butyrolactone, epsilon-decalactone, 2,5-diketomorpholine, pivalolactone, alpha,alpha-diethylpropiolactone, ethylene carbonate, ethylene oxalate; 3-methyl-1,4-dioxane-2,5-dione, 3,3-diethyl-1,4-dioxan-2,5-dione, gamma-butyrolactone, 1,4-dioxepan-2-one, 1,5-dioxepan-2-one, 1,4-dioxan-2-one, 6,8-dioxabicycloctane-7-one, and combinations thereof.

4. The method according to claim 1, wherein the polycondensation polyester comprises the reaction product of diglycolic acid and/or a derivative thereof, up to about 25 mole percent of an aliphatic diacid based on the total moles of acid, and ethylene glycol.

5. The method according to claim 1, wherein the medical device having as one of its component a co-polyester comprising the reaction product of a polycondensation polyester and at least one lactone, is placed over tissue that has been sutured or repaired with a mesh.

6. The method according to claim 1, wherein the medical device is sterilized gamma or electron beam sterilized.

* * * * *